United States Patent [19]
Klein

[11] Patent Number: 5,682,607
[45] Date of Patent: Nov. 4, 1997

[54] SKIN APPLIQUE TO PROVIDE PROTECTION FROM ULTRAVIOLET LIGHT

[76] Inventor: Jeffrey A. Klein, 30280 Rancho Viejo Rd., San Juan Capistrano, Calif. 92675

[21] Appl. No.: 746,715

[22] Filed: Nov. 15, 1996

[51] Int. Cl.⁶ .................................................. A41D 13/00
[52] U.S. Cl. ........................................ 2/9; 2/206; 128/858
[58] Field of Search ........................... 2/9, 206, 455, 2/15, 174; 128/857, 858, 888; 428/40.1, 41.7, 41.8, 41.9; 602/41, 52, 54, 57, 74

[56] References Cited

U.S. PATENT DOCUMENTS

| | | | |
|---|---|---|---|
| 1,354,652 | 10/1920 | Jefferies | 128/857 |
| 1,761,664 | 6/1930 | Harris | 2/206 |
| 3,068,863 | 12/1962 | Bowman | 128/858 |
| 3,092,103 | 6/1963 | Mower | 128/858 |
| 3,594,813 | 7/1971 | Sanderson | 2/9 |
| 4,674,133 | 6/1987 | Oschner | 2/9 |
| 4,719,909 | 1/1988 | Micchia et al. | 128/858 |
| 4,745,916 | 5/1988 | Seber | 2/15 |
| 4,944,040 | 7/1990 | Riedel et al. | 128/858 |
| 4,979,811 | 12/1990 | Boyer | 128/858 |
| 5,167,036 | 12/1992 | Daprato | 2/2 |
| 5,191,897 | 3/1993 | Meshel | 128/858 |
| 5,243,708 | 9/1993 | Vanuch | 2/206 |
| 5,274,847 | 1/1994 | Lauttamus | 2/9 |
| 5,416,923 | 5/1995 | Peugh | 2/206 |
| 5,592,687 | 1/1997 | Lajeunesse | 2/206 |

*Primary Examiner*—Amy B. Vanatta
*Attorney, Agent, or Firm*—Stetina Brunda Garred & Brucker

[57] ABSTRACT

A skin applique protector protects a selected area of a user's skin from harmful effects of overexposure to ultraviolet light. The skin applique protector has a sheet of flexible material, a first layer of adhesive formed upon a first surface of the sheet of flexible material, and a second layer of adhesive formed upon a second surface of the sheet of flexible material. A first sheet of peel-away material generally covers the first layer of adhesive and a second sheet of peel-away material generally covers the second layer of adhesive material. Either the sheet of flexible material or the first layer of adhesive contains an ultraviolet light blocking material. Application of the sheet of flexible material to the selected area of the user's skin inhibits overexposure of the user's skin to harmful ultraviolet light.

35 Claims, 1 Drawing Sheet

SKIN APPLIQUE TO PROVIDE PROTECTION FROM ULTRAVIOLET LIGHT

FIELD OF THE INVENTION

The present invention relates generally to means for protecting a user's skin from sunlight. It relates more particularly to a skin applique protector for protecting a selected area of a user's skin from the harmful effects of overexposure to ultraviolet light.

BACKGROUND OF THE INVENTION

In recent years it has become widely accepted by both the medical community and general population that overexposure to ultraviolet light can have a seriously detrimental impact upon a person's health. Even infrequent overexposure to ultraviolet light is known to cause the formation actinic keratoses, which are known to be precancerous in nature.

As is well known, certain areas of the human body are particularly susceptible to such overexposure to ultraviolet light. This is generally due to their position and orientation upon the body. For example, the nose is one such area which is particularly susceptible to the harmful effects of ultraviolet light. This occurs because the nose is positioned and oriented such that it is generally exposed to direct ultraviolet light when a person participates in outdoor activities.

Creams, lotions, ointments, and the like, herein collectively referred to as ointments, for protecting a user's skin from the harmful effects of overexposure to ultraviolet light are well known. Such ointments commonly comprise an ultraviolet light blocking agent of varying effectiveness in preventing the transmission of harmful ultraviolet light therethrough.

Even the more effective of such ointments is subject to undesirable rubbing off or washing away, particularly when utilized by those participating in vigorous outdoor activities and/or water activities. It is not at all uncommon for a user to properly apply an otherwise effective ointment to those areas of the user's body most prone to receive excessive ultraviolet light, only to have the ointment rub off or wash away, thus resulting in a painful and potentially dangerous overexposure to ultraviolet light or sunburn.

In view of the deficiencies of such prior art ointments to maintain their effectiveness, particularly when utilized by a person who is active or participating in water activities, various other means for preventing overexposure to ultraviolet light have been attempted. Such other means for preventing overexposure to ultraviolet light generally involve the use of a mechanical device to shade or cover a portion of the user's body, e.g., the user's nose, from the sun.

Examples of such prior art devices for preventing undesirable overexposure of a person's nose to ultraviolet light include those disclosed in U.S. Pat. No. 1,761,665 issued on Jun. 3, 1930 to Harris and entitled NOSE PROTECTOR; U.S. Pat. No. 3,594,813 issued on Jul. 27, 1971 to Sanderson and entitled PROTECTIVE DEVICE; U.S. Pat. No. 4,674,133 issued on Jun. 23, 1987 to Oschner and entitled ULTRAVIOLET NOSE PROTECTOR; U.S. Pat. No. 5,167,036 issued on Dec. 1, 1992 to Daprato and entitled NOSE PROTECTOR; U.S. Pat. No. 5,243,708 issued on Sep. 14, 1993 to Vanuch and entitled DISPOSABLE SCENTED MASK; and U.S. Pat. No. 5,274,847 issued Jan. 4, 1994 to Lauttamus on and entitled NOSE PROTECTOR.

Although such prior art mechanical devices are generally extremely effective in blocking ultraviolet light, and are not generally susceptible to rubbing or washing off, all such prior art devices possess inherent deficiencies which detract from their overall desirability. For example, such prior art devices are generally very prominent in appearance, and thus objectionable to most potential users. It is well known that most people would prefer a means for protecting themselves from the undesirable effects of ultraviolet light which is not aesthetically undesirable. In this respect, it is generally desirable that the device be as inconspicuous as possible.

Although various attempts have been made to form such mechanical protectors in a manner which is aesthetically acceptable, such practice is, to date, excessively complex and of dubious benefit. This is exemplified by the teaching of U.S. Pat. No. 3,594,813, which involves the molding of a device into the shape of the body portion, e.g., the nose, of the user, and then requires the manual application of an adhesive to the inner surface of the device.

Thus, as will be appreciated by those skilled in the art, far more effort is required in the practice of this device than is deemed generally acceptable. Further, since this device is intended to be durable enough to survive repeated wearings and washings, it must be of sufficient thickness to be readily visible when worn by a user. The requirement for such thickness generally obviates any benefit derived from construction of the device in a manner which mimics the shape of the body portion to be covered thereby.

In view of the deficiencies of the prior art, it is beneficial to provide means for protecting a selected area of a user's skin from the harmful effects of overexposure to ultraviolet light which is effective, durable, and which is also aesthetically acceptable.

SUMMARY OF THE INVENTION

The present invention specifically addresses and alleviates the deficiencies associated with the prior art. More particularly, the present invention comprises a skin applique protector for protecting a selected area of a user's skin from the harmful effects of overexposure to ultraviolet light. Thus, the formation of actinic keratoses, and their inherent potential for forming cancerous lesions, is mitigated.

The skin applique protector comprises a sheet of flexible material, a first layer of adhesive formed upon a first surface of the sheet of flexible material, and a second layer of adhesive formed upon a second surface of the sheet of flexible material. A first sheet of peel-away material generally covers the first layer of adhesive and a second sheet of peel-away material generally covers the second layer of adhesive. Thus, the adhesive covered sheet of flexible material is sandwiched between the two peel-away layers, so as to prevent soiling or other degradation of the adhesive layers. The sheet of flexible material and/or the first layer of adhesive comprises an ultraviolet light blocking material, so as to mitigate the amount of ultraviolet light to which the user's skin is exposed.

According to the preferred embodiment of the present invention the sheet of flexible material comprises a very thin sheet of polymer material, clear or transparent to visible light, preferably approximately 0.0005 to 0.005 inch in thickness.

In one alternative configuration of the present invention, the ultraviolet light blocking material is an additive which is mixed with the polymer material during the formation thereof. In another alterative configuration, the ultraviolet light blocking material is formed as a separate coating or layer upon the sheet of flexible material.

Preferably, the sheet of flexible material is cut or otherwise formed so as to have a shape compatible with use upon a particular portion of the user's body, e.g., the nose. Thus, the sheet of flexible material has a generally triangular shape, for example, which is formed to substantially cover part or all of the user's nose. Those skilled in the art will appreciate the various other shapes and configurations of the sheet of flexible material are likewise suitable for covering various other areas of the user's body.

The sheet of flexible material may be formed into the desired shape via laser cutting, die cutting, or any other such contemporary process.

The sheet of flexible material is formed so as to be generally transparent to visible light, and is thus difficult to detect. As such, the skin applique protector of the present invention is aesthetically acceptable, particularly as compared with prior art devices. Indeed, the skin applique protector of the present invention is less noticeable than some prior art ointments.

Preferably, the sheet of flexible material is formed so as to be generally permeable to water. Thus, excessive hydration or maceration of the skin covered by the skin applique protector of the present invention is prevented. The sheet of flexible material is preferably formed to be generally permeable to water by providing micro-perforations which facilitate water flow therethrough.

One method by which such micro-perforations are provided is by utilizing a porous woven material. Another method by which such micro-perforations are provided is by forming the micro-perforations within an otherwise generally non-porous flexible material via a laser. Yet another method by which such micro-perforations are provided is by forming the flexible material such that it is comprised of a porous or spongeform material.

According to the preferred embodiment of the present invention, the first layer of adhesive comprises a comparatively strong adhesive for assuring positive attachment of the sheet of flexible material to the user's skin. Thus, the skin applique protector of the present invention may be utilized by a user participating in various physical activities, including water sports or other such activities, which would tend to wash off prior art ointments. The comparatively strong adhesive assures that the skin applique protector of the present invention remains in place if physically abraded or if exposed to water.

The second layer of adhesive preferably comprises a comparatively weak adhesive which allows the second peel-away layer to easily be removed therefrom during application.

The first and second peel-away layers preferably comprise the release paper.

The sheet of flexible material and the first adhesive are preferably formed of a hypo-allergenic material such that they do not cause an adverse reaction in sensitive individuals.

It is contemplated that the skin applique protector of the present invention may be formed of a single layer of flexible material. Alternatively, a plurality of such layers may be utilized so as to provide enhanced strength and/or other desirable properties. For example, one layer may contain an ultraviolet blocking agent which is particularly effective for ultraviolet A, while another layer contains an ultraviolet blocking agent which is particularly effective for ultraviolet B.

The skin applique of the present invention is suitable for use in a variety of other applications. For example, the skin applique protector can be utilized to protect selected areas of a user's skin from environmental conditions other than ultraviolet light. The skin applique protector of the present invention provides protection from wind, cold weather, dust, sand, and/or various other environmental contaminants. Further, the skin applique protector may be utilized in post-operative applications, so as to maintain cleanliness by isolating the selected area from the environment.

These, as well as other advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENT

The detailed description set forth below in connection with the appended drawings is intended as description of the presently preferred embodiment of the invention and is not intended to represent the only form in which the present invention may be constructed or utilized. The description sets forth the function and the sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
FIG. 1 is a perspective view of the person's face having the skin applique protector of the present invention placed over the nose thereof.
Figure 2:
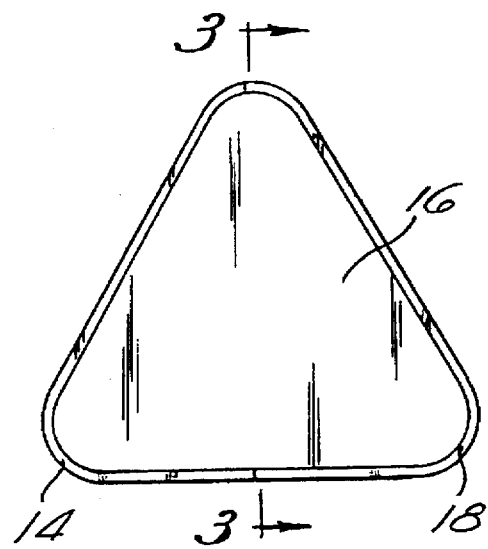
FIG. 2 is a top view of the skin applique protector of the present invention.

The present invention is generally illustrated in FIGS. 1–4, which show a presently preferred embodiment thereof. Referring now to FIG. 1, the skin applique protector of the present invention generally comprises a sheet of flexible material 10 configured to be placed upon a desired area of the user's skin, such as the user's nose 12. Although the descriptions and drawings of the subject patent application discuss and illustrate a skin applique protector specifically configured to be utilized upon a user's nose, such discussion and illustration is by way of example only, and not by way of limitation. Those skilled in the art will appreciate that the skin applique protector of the present invention may be utilized upon various different portions of a user's body. For example, the skin applique protector of the present invention may be specifically configured so as to cover the back of a user's neck, a user's shoulders, a user's forehead or selected portions of a user's arms and/or legs. Indeed, the skin applique protector of the present invention may be specifically configured so as to cover any desired portion of a user's body.

The skin applique protector of the present invention further comprises a first peel-away layer or release paper 14, which, when peeled-away from the flexible substrate 10 exposes a first layer of adhesive formed upon the flexible substrate 10 for attaching the flexible substrate 10 to the user's nose 12.

Figure 4:
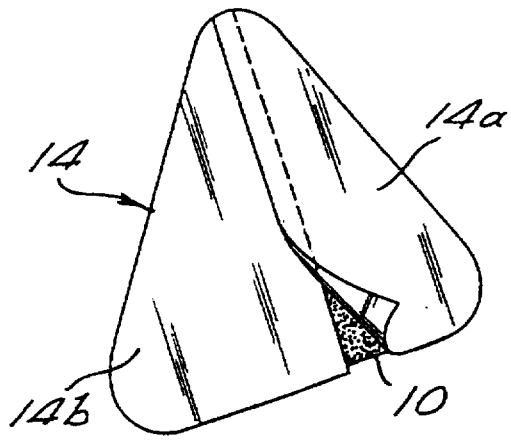
FIG. 4 is a perspective view of the skin applique protector of the present invention showing a portion of the first peel-away layer being removed therefrom.

With particular reference to FIG. 4, the first release paper 14 preferably comprises first 14a and second 14b separate portions thereof, so as to facilitate ease in removal from the sheet of flexible material 10. Thus, to remove the first release paper 14, in preparation for application of the sheet of flexible material to the user's nose, the user merely peels-away the first portion 14a thereof, thereby exposing approximately one-half of the first layer of adhesive. The skin applique protector of the present invention may then be positioned upon the user's nose 12, as desired, and then the second portion 14b of the release paper peeled-away from the sheet of flexible material 10. The use of the skin applique protector is described in detail below.

In a similar manner, the skin applique protector of the present invention further comprises a second peel-away layer or release paper 16, which, when peeled away from the flexible substrate 10 exposes a second layer of adhesive formed upon the flexible substrate 10 for attaching the flexible substrate 10 to the second release paper 16. The second release paper 16 aides in handling the very thin sheet of flexible material 10. Preferably, the second release paper 16 is formed in two sections, in a manner similar to that of the first release paper 14, and is removable from the sheet of flexible material 10 in a similar manner. As those skilled in the art will appreciate, the release papers 14, 16 may alternatively comprise a polymer material, preferably having a thickness which is greater than the thickness of the flexible substrate 10. The flexible material 10, the first release paper 14, and the second release paper 16 are all preferably die-cut from sheet stock.

Figure 3:
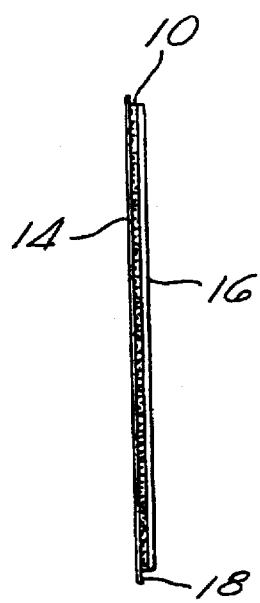
FIG. 3 is a cross-sectional side view taken along lines 3 of FIG. 2.

With particular reference to FIG. 3, the skin applique protector of the present invention thus generally comprises the sheet of flexible material 10 sandwiched between the first peel-away layer 14 and a second peel-away layer 16. Thus, the adhesive formed upon the first side of the sheet of flexible material 10 holds the first release paper 14 thereto and the adhesive formed upon the second side of the sheet of flexible material 10 holds the second release paper 16 thereto.

The sheet of flexible material 10 preferably comprises a polymer material which is generally transparent to visible light, so as to increase the aesthetic desirability thereof.

Preferably, the first release paper 14 is formed to have slightly greater surface area than the second release paper 16, so as to form a peripheral portion 18 of the first release paper 14. The peripheral portion 18 both aides in the identification of the first release paper 14 and also aides in removal thereof, by providing an easy means for grasping thereof.

An ultraviolet light blocking agent is either present in the first adhesive, integrated within the sheet of flexible material 10, or formed upon either the first or second surface of the sheet of flexible material 10. Thus the ultraviolet light blocking agent is present in the skin applique protector when it is applied to the user's nose 12. The ultraviolet light blocking agent preferably substantially attenuates both ultraviolet A and ultraviolet B light.

The use of a sheet of flexible material 10 which is generally transparent to visible light makes the skin applique protector of the present invention difficult to see when used, thereby providing aesthetic appeal. The generally transparent flexible material 10 allows the natural skin tone of the user to be seen therethrough, thus making the skin applique protector substantially inconspicuous.

According to the preferred embodiment of the present invention, the sheet of flexible material is generally permeable to water, so as to prevent excess hydration and/or maceration of the skin to which the skin applique protector is attached. Thus, as the user participates in vigorous activities, perspiration does not tend to build up beneath the skin applique protector of the present invention. Further, when exposed to water, such as when the user participates in water activities, the skin applique protector of the present invention and the skin therebeneath tends to dry quickly when the user leaves the water.

Such permeability of the sheet of flexible material 10 also helps maintain the skin applique protector of the present invention in place upon the user, by allowing both the skin applique protector and the skin therebeneath to dry out, such that the adhesive holding the sheet of flexible material to the skin is not adversely affected by the moisture.

Such water permeability may be provided via micro-perforations formed within the sheet of flexible material 10, which allow water flow therethrough. Such micro-perforations may be provided via the use of a porous woven material or, alternatively, may be formed within the sheet of flexible material 10 via laser cutting and/or the use of a spongeform material, such as an open cell polymer.

The first layer of adhesive is preferably comparatively stronger than the second layer thereof, so as to facilitate reliable attachment of the sheet of flexible material 10 to the user's skin. The use of a comparatively weaker adhesive utilized to attach the second release paper 16 to the sheet of flexible material 10 facilitates easy removal of second release paper 16 from the sheet of flexible material 10.

The sheet of flexible material 10, the first release paper 14 and the second release paper 16 may all be formed, so as to have generally complimentary shapes, via die cutting, laser cutting, or various other contemporary means.

Both the sheet of flexible material and the first adhesive are preferably formed of hypo-allergenic material, so as to facilitate use of the skin applique protector of the present invention by sensitive individuals.

Having described the structure of the skin applique protector of the present invention, it may be beneficial to describe the use thereof. The user merely peels-away the first 14a portion of the first release paper 14, thereby exposing approximately one-half of the sheet of flexible material 10 therebeneath, having the first adhesive formed thereupon. The skin applique protector may then be positioned, as desired, upon the user's nose 12 and attached thereto by pressing firmly against the second release paper 16. Once positioned properly and adhered at least partly in position, the second portion 14b of the first release paper 14 is peeled-away from the sheet of flexible material 10 and the remainder of the sheet of flexible material 10 is adhered to the user's nose.

After the entire sheet of flexible material 10 has been adhered to the user's nose 12, then the second release paper 16 is peeled-away from the sheet of flexible material 10, so as to leave only the sheet of flexible material 10, which is generally transparent to visible light upon the user's nose 12. Thus, the skin applique protector of the present invention is not readily apparent to one who casually observes a user, thereby increasing its aesthetic appeal.

The skin applique protector of the present invention may be formed to have a shape for a specific body portion, e.g., the nose. Alternatively, the skin applique protector may be provided in sheet form and then cut to any desired shape by the user, with scissors, for example.

It is understood that the exemplary skin applique protector described herein and shown in the drawings represents only a presently preferred embodiment of the invention. Indeed, various modifications and additions may be made to such embodiment without departing from the spirit and scope of the invention. For example, the use of various different generally transparent materials is contemplated. Also, those skilled in the art will appreciate that various thicknesses and types of peel-away material are suitable for use in the practice of the present invention.

Thus, these and other modifications and additions may be obvious to those skilled in the art and may be implemented to adapt the present invention for use in a variety of different applications.

What is claimed is:

1. A skin applique protector for protecting a selected area of a user's skin from harmful effects of overexposure to ultraviolet light, said protector comprising:
   a) a sheet of flexible material;
   b) a first layer of adhesive formed upon a first surface of said sheet of flexible material;
   c) a second layer of adhesive formed upon a second surface of said sheet of flexible material;
   d) a first sheet of peel-away material generally covering said first layer of adhesive;
   e) a second sheet of peel-away material generally covering said second layer of adhesive material;
   f) wherein at least one of said sheet of flexible material and said first layer of adhesive comprises an ultraviolet light blocking material; and
   g) wherein application of said sheet of flexible material to the selected area of the user's skin inhibits overexposure thereof to harmful ultraviolet light.

2. The skin applique protector as recited in claim 1, wherein said sheet of flexible material comprises a polymer material.

3. The skin applique protector as recited in claim 1, wherein said sheet of flexible material comprises a polymer material comprising an ultraviolet light blocking additive.

4. The skin applique protector as recited in claim 1, wherein said sheet of flexible material comprises a polymer material having an ultraviolet light blocking material formed thereon.

5. The skin applique protector as recited in claim 1, wherein said sheet of flexible material is specifically formed to have a shape compatible with use upon a particular portion of a user's body.

6. The skin applique protector as recited in claim 1, wherein said sheet of flexible material is formed to have a shape compatible with use upon a user's nose.

7. The skin applique protector as recited in claim 1, wherein said sheet of flexible material is generally transparent to visible light.

8. The skin applique protector as recited in claim 1, wherein said sheet of flexible material is generally permeable to water.

9. The skin applique protector as recited in claim 1, wherein said sheet of flexible material comprises micro-perforations to facilitate water flow therethrough.

10. The skin applique protector as recited in claim 1, wherein said sheet of flexible material comprises a porous woven material.

11. The skin applique protector as recited in claim 1, wherein said sheet of flexible material comprises laser cut micro-pores.

12. The skin applique protector as recited in claim 1, wherein said sheet of flexible material comprises micro-pores defined by a spongeform material.

13. The skin applique protector as recited in claim 1, wherein said first layer of adhesive comprises an ultraviolet light blocking material.

14. The skin applique protector as recited in claim 1, wherein:
   a) said first layer of adhesive comprises a comparatively strong adhesive; and
   b) said second layer of adhesive comprises a comparatively weak adhesive.

15. The skin applique protector as recited in claim 1, wherein at least one of said first and second sheets of peel-away material comprises release paper.

16. The skin applique protector as recited in claim 1, wherein said sheet of flexible material and said first adhesive are hypo-allergenic.

17. The skin applique protector as recited in claim 1, wherein said sheet of flexible material, said first sheet of peel-away material, and said second sheet of peel-away material are generally triangular in configuration.

18. A method for forming a skin applique protector for protecting a selected area of a user's skin from harmful effects of overexposure to ultraviolet light, said method comprising the steps of:
   a) forming a sheet of flexible material;
   b) forming a first layer of adhesive upon a first surface of the sheet of flexible material;
   c) forming a second layer of adhesive upon a second surface of the sheet of flexible material;
   d) generally covering the first layer of adhesive with a first sheet of peel-away material;
   e) generally covering the second layer of adhesive with a second sheet of peel-away material; and
   f) wherein at least one of said sheet of flexible material and said first layer of adhesive comprises an ultraviolet light blocking material.

19. The method as recited in claim 18, wherein the step of forming a sheet of flexible material comprises die-cutting the flexible material.

20. The method as recited in claim 18, wherein the step of forming a sheet of flexible material comprises laser cutting the flexible material.

21. The method as recited in claim 18, wherein the step of forming a sheet of flexible material comprises forming a sheet of flexible polymer material.

22. The method as recited in claim 18, wherein the step of forming a sheet of flexible material comprises forming a sheet of flexible material comprising an ultraviolet light blocking additive.

23. The method as recited in claim 18, wherein the step of forming a sheet of flexible material comprises forming a layer of ultraviolet light blocking material upon the sheet of flexible material.

24. The method as recited in claim 18, wherein the step of forming a sheet of flexible material comprises forming a sheet of flexible material having a shape compatible with use upon a particular portion of the user's body.

25. The method as recited in claim 18, wherein the step of forming a sheet of flexible material comprises forming a sheet of flexible material having a shape compatible with use upon a user's nose.

26. The method as recited in claim 18, wherein the step of forming a sheet of flexible material comprises forming a sheet of flexible material which is generally transparent to visible light.

27. The method as recited in claim 18, wherein the step of forming a sheet of flexible material comprises forming a sheet of flexible material which is generally permeable to water.

28. The method as recited in claim 18, wherein the step of forming a sheet of flexible material comprises forming a sheet of flexible material having micro-perforations formed therein.

29. The method as recited in claim 18, wherein the step of forming a sheet of flexible material comprises forming a sheet of flexible material comprised of a porous woven material.

30. The method as recited in claim 18, wherein the step of forming a sheet of flexible material comprises forming micro-pores within the sheet of flexible material via a laser.

31. The method as recited in claim 18, wherein the step of forming a sheet of flexible material comprises forming a sheet of flexible material comprised of a spongeform material.

32. The method as recited in claim 18, wherein the step of forming a first layer of adhesive upon a first surface of the sheet of flexible material comprises forming a first layer of adhesive comprising an ultraviolet light blocking material upon the first surface of the sheet of flexible material.

33. The method as recited in claim 18, wherein the steps of forming a first layer of adhesive upon a first surface of the sheet of flexible material and forming a second layer of adhesive upon the second surface of the sheet of flexible material comprises forming a first layer of comparatively strong adhesive upon the first surface of the sheet of flexible material and forming a second layer of comparatively weak adhesive upon the second surface of the sheet of flexible material.

34. The method as recited in claim 18, wherein at least one of the steps of generally covering the first layer of adhesive with a first sheet of peel-away material and generally covering the second layer of adhesive with a second sheet of peel-away material comprises generally covering at least one of the first and second layers of adhesive material with release paper.

35. The method as recited in claim 18, wherein the steps of forming a sheet of flexible material and forming a first layer of adhesive upon a first surface upon the sheet of flexible material comprise forming a sheet of flexible material comprised of a hypo-allergenic material and forming a first layer of adhesive formed of hypo-allergenic material.

* * * * *